United States Patent
Moghe et al.

(10) Patent No.: US 9,402,770 B2
(45) Date of Patent: Aug. 2, 2016

(54) ANTIMICROBIAL NON-ADHERENT DRESSINGS AND RELATED METHODS THEREFOR

(71) Applicant: COVIDIEN LP, Mansfield, MA (US)

(72) Inventors: Ajit Moghe, Bellingham, MA (US); Anand Kanchagar, Auburn, MA (US)

(73) Assignee: COVIDIEN, Mansfield, MA (US)

( * ) Notice: Subject to any disclaimer, the term of this patent is extended or adjusted under 35 U.S.C. 154(b) by 62 days.

(21) Appl. No.: 13/746,012

(22) Filed: Jan. 21, 2013

(65) Prior Publication Data

US 2013/0150765 A1 Jun. 13, 2013

Related U.S. Application Data

(63) Continuation-in-part of application No. 13/316,028, filed on Dec. 9, 2011.

(51) Int. Cl.
A61F 13/00 (2006.01)

(52) U.S. Cl.
CPC ..... *A61F 13/00063* (2013.01); *A61F 13/00991* (2013.01); *A61F 2013/00161* (2013.01); *A61F 2013/00519* (2013.01)

(58) Field of Classification Search
CPC ... A61K 8/028; A61K 9/7061; A61K 9/7084; A61L 15/28; A61L 15/44; A61L 15/46; A61F 13/00; A61F 13/0063; A61F 13/00991; A61F 2013/00519; A61F 2013/00161
USPC ........ 602/41–59; 424/443–449; 604/304–308
See application file for complete search history.

(56) References Cited

U.S. PATENT DOCUMENTS

| | | | |
|---|---|---|---|
| 1,661,879 A | | 3/1928 | De Goncz |
| 2,423,707 A | | 7/1947 | Kenyon et al. |
| 2,764,976 A | * | 10/1956 | Skiles, Jr. et al. ............... 602/51 |
| 2,804,424 A | * | 8/1957 | Stirn et al. .................... 424/446 |
| 3,400,004 A | | 9/1968 | Corry |
| 3,545,442 A | | 12/1970 | Wicker et al. |
| 3,592,909 A | | 7/1971 | Pritchard |
| 3,776,857 A | * | 12/1973 | Linder ........................... 516/29 |
| 3,837,344 A | | 9/1974 | Patience |

(Continued)

FOREIGN PATENT DOCUMENTS

| | | |
|---|---|---|
| DE | 29723320 U1 | 8/1998 |
| EP | 0531096 A2 | 3/1993 |

(Continued)

OTHER PUBLICATIONS

Tyco Healthcare, Kendall Material Saftey Data Sheet, Vaseline Oil Emulsion Dressing, Jan. 30, 2004.*

(Continued)

*Primary Examiner* — Kim M Lewis

(57) ABSTRACT

A wound dressing comprising a substrate comprising a plurality of fibers, at least one antimicrobial agent in the substrate, and an oil emulsion on at least a portion of the substrate is disclosed. The at least one antimicrobial agent can be polyhexamethylene biguanide, and the oil emulsion can consist essentially of a petrolatum in a range of from about 75 wt % to about 90 wt % of the oil emulsion, a mineral oil in a range of from about 10 wt % to about 20 wt % of the oil emulsion, water in a range of from about 0.1 wt % to about 1 wt % of the oil emulsion, and at least one surfactant in a range of from about 1 wt % to about 5 wt % of the oil emulsion.

13 Claims, 4 Drawing Sheets

(56) References Cited

U.S. PATENT DOCUMENTS

| | | | |
|---|---|---|---|
| 4,203,435 A | 5/1980 | Krull et al. | |
| 4,214,582 A | 7/1980 | Patel | |
| 4,363,322 A | 12/1982 | Andersson | |
| 4,373,519 A | 2/1983 | Errede et al. | |
| 4,541,426 A | 9/1985 | Webster | |
| 4,832,858 A * | 5/1989 | Vishnupad et al. | 508/110 |
| 4,984,570 A | 1/1991 | Langen et al. | |
| 5,075,151 A | 12/1991 | Kufner et al. | |
| 5,135,472 A | 8/1992 | Hermann et al. | |
| 5,422,117 A * | 6/1995 | Morton | A61K 9/0031 424/436 |
| 5,465,735 A | 11/1995 | Patel | |
| 5,607,760 A * | 3/1997 | Roe | 442/375 |
| 5,632,731 A | 5/1997 | Patel | |
| 5,652,049 A | 7/1997 | Suzuki | |
| 5,814,031 A | 9/1998 | Mooney et al. | |
| 5,879,487 A | 3/1999 | Ravella | |
| 5,941,840 A | 8/1999 | Court et al. | |
| 6,333,093 B1 | 12/2001 | Burrell et al. | |
| 6,369,289 B1 | 4/2002 | Orr, III | |
| 6,605,751 B1 | 8/2003 | Gibbins et al. | |
| 6,700,032 B1 | 3/2004 | Gray | |
| 8,088,964 B2 | 1/2012 | Mouton | |
| 2003/0097103 A1 | 5/2003 | Horney et al. | |
| 2003/0190853 A1 | 10/2003 | Lovingood | |
| 2004/0081817 A1* | 4/2004 | Tanaka et al. | 428/317.9 |
| 2005/0058683 A1* | 3/2005 | Levy et al. | 424/423 |
| 2006/0240083 A1 | 10/2006 | Klein et al. | |
| 2007/0128258 A1* | 6/2007 | Faure et al. | 424/445 |
| 2007/0237812 A1 | 10/2007 | Patel et al. | |
| 2010/0036334 A1 | 2/2010 | Heagle et al. | |
| 2012/0165434 A1* | 6/2012 | Martin | 524/58 |
| 2012/0294920 A1 | 11/2012 | Gorka | |
| 2012/0294927 A1 | 11/2012 | Gorka | |
| 2012/0323205 A1* | 12/2012 | Vanderwagen et al. | 604/385.06 |

FOREIGN PATENT DOCUMENTS

| | | | |
|---|---|---|---|
| EP | 1216319 A1 | | 6/2002 |
| GB | 899965 A | | 6/1962 |
| GB | 1406669 A | | 9/1975 |
| GB | 1445247 | * | 8/1976 |
| GB | 2132939 A | | 7/1984 |
| GB | 2194446 A | | 3/1988 |
| GB | 2321216 A | | 7/1998 |
| WO | 96/07783 A1 | | 3/1996 |
| WO | 00/78883 A1 | | 12/2000 |
| WO | 0123653 A1 | | 4/2001 |
| WO | 01/45615 A1 | | 6/2001 |
| WO | 01/74300 A1 | | 10/2001 |
| WO | 2013/085640 A1 | | 6/2013 |

OTHER PUBLICATIONS

Kendall, Material Saftey Data Sheet, Curity Xeroform Petrolatum Dressing, Sep. 14, 1999.*

Kirker et al., Efficacy of Polyhexamethylene Biguanide-containing Antimcrobial Foam Dressing Agains MRSA Relative to Standard Foam Dressing, 2009, Wounds, 21(9), 229-233.*

International Search Report corresponding to PCT Appl. No. PCT/US2014/012014 dated Mar. 14, 2014.

EP Examination Report from Application No. 11 172 433.2 dated Dec. 9, 2013.

Chinese Office Action from Application No. CN200980139019.1 dated Feb. 26, 2014.

Office Action from U.S. Appl. No. 13/316,028, dated Jul. 1, 2014, 10 pp.

Patent Examination Report No. 1 from Counterpart Patent Application No. 2012348349, dated Sep. 8, 2014, 3 pp.

Second Written Opinion from Counterpart International Application No. PCT/US2014-012014, mailed Jan. 8, 2015, 6 pp.

Final Office Action from U.S. Appl. No. 13/316,028, dated Feb. 23, 2015, 11 pp.

Written Opinion from Counterpart International Patent Application No. PCT/US2014/012014, dated Jan. 8, 2015, 6 pp.

Notification of the First Office Action, and translation thereof, from Counterpart Chinese Patent Application No. 201280060499A, dated Dec. 3, 2014, 16 pp.

Office Action from U.S. Appl. No. 13/316,028, dated Apr. 21, 2015, 9 pp.

Extended Search Report from European Application No. 12855165.2, dated Jul. 2, 2015, 7 pp.

International Preliminary Report on Patentability from Counterpart International Patent Application No. PCT/US2014/012014, mailed Mar. 31, 2015, 15 pp.

Office Action from U.S. Appl. No. 13/316,028, dated Sep. 24, 2015, 12 pp.

Examination Report from Canadian Patent Application No. 2,857,956, dated Apr. 10, 2015, 4 pp.

* cited by examiner

ANTIMICROBIAL NON-ADHERENT DRESSINGS AND RELATED METHODS THEREFOR

CROSS-REFERENCE TO RELATED APPLICATION

This application is a continuation-in-part application of and claims the benefit of priority under 35 U.S.C. §120 to co-pending U.S. patent application Ser. No. 13/316,028, titled NON-ADHERENT WOUND DRESSINGS AND RELATED METHODS THEREFOR, filed on Dec. 9, 2011, which is incorporated herein by reference in its entirety for all purposes.

TECHNICAL FIELD

The present disclosure relates to substrates such as fabrics, and more particularly, to wound dressings including substrates formed with fibers impregnated with an oil emulsion and an antimicrobial agent and exhibit none or low adherency to wounds.

BACKGROUND

Wound dressings have been used in the medical industry to protect and to facilitate healing of open wounds. Wound dressings are generally placed over a wound to protect and promote healing of the wound. In the case of exuding wounds, such as pressure sores, ulcers, and burns, it is customary to provide a dressing having an absorbent material for absorbing at least a portion of the wound exudates as it is produced. Absorbing exudates promotes healing by removing potentially harmful bacteria from the wound bed, and also prevents damage to the surrounding skin that can be caused by an excessively moist environment. The absorbent material temporarily stores the excess exudates until removal thereof, typically periodically and replaced with a new dressing.

Woven gauze fabric has been used as a wound dressing to absorb wound exudates and to protect the wound from unwanted environmental factors. Such fabric is loosely woven and includes yarns made of cellulosic fibers, such as cotton and viscose rayon. The absorbency characteristics of the dressing depend on the material of construction. For example, the absorbency capacity of gauze relates to the characteristics of interstices within the yarn and between successive yarns.

Some absorbent materials utilized in some wound dressings, such as cotton, tend to become attached to a healing wound bed and may shed small fibers into the wound that may remain in the wound when the dressing is changed. Removing the dressing and/or stray fibers can be a labor intensive procedure that may further damage the wound, and neglecting to remove stray fibers may cause irritation or result in granuloma formation and otherwise inhibit natural healing of the wound.

SUMMARY

One or more aspects of the disclosure can be directed to a wound dressing. The wound dressing can comprise a substrate comprising a plurality of fibers, at least one antimicrobial agent in the substrate, and an oil emulsion on at least a portion of the substrate. In one or more embodiments pertinent to one or more aspects of the disclosure, the at least one antimicrobial agent is a biguanide and, in some cases, the oil emulsion consists essentially of a petrolatum in a range of from about 75 wt % to about 90 wt % of the oil emulsion, a mineral oil in a range of from about 10 wt % to about 20 wt % of the oil emulsion, water in a range of from about 0.1 wt % to about 1 wt % of the oil emulsion, and at least one surfactant in a range of from about 1 wt % to about 5 wt % of the oil emulsion. In one or more embodiments pertinent to one or more aspects of the present disclosure, the at least one surfactant is at least one of an anionic surfactant selected from the group consisting of sodium dodecylsulfate, sodium dodecylbenzene sulfonate, sodium dodecylnaphthalene sulfate, abitic acid, alkyldiphenyloxide disulfonate, sodium dodecylbenzene sulfonate, and combinations thereof; a cationic surfactant selected from the group consisting of alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, dodecylbenzyl triethyl ammonium chloride, and combinations thereof; and a nonionic surfactant selected from the group consisting of polyacrylic acid, methalose, methyl cellulose, ethyl cellulose, propyl cellulose, hydroxyethyl cellulose, carboxymethyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, sorbitan sesquioleate, polyoxyethylene stearyl ether, polyoxyethylene nonylphenyl ether, dialkylphenoxy poly (ethyleneoxy)ethanol, and combinations thereof. In one or more embodiments pertinent to one or more aspects of the present disclosure, the at least one antimicrobial agent is polyhexamethylene biguanide in a range of from about 500 parts per million (ppm) to less than about 1,500 ppm on the substrate; and in some cases, the at least one antimicrobial agent is polyhexamethylene biguanide present in a range of from about 1,500 ppm to about 3,500 ppm on the substrate. In one or more embodiments pertinent to one or more aspects of the present disclosure, the substrate comprises a plurality of first yarns comprising the plurality of cellulosic fibers and a plurality of second fibers comprising a non-adherent polymeric material selected from the group consisting of polyethylene, polypropylene, polyfluoroethylene, polyfluoropropylene, polyfluoropolyethylene glycol, polytetrafluoroethylene, polyethylene terephthalate, polyethylene naphthalate, polytrimethylene terephthalate, polybutylene terephthalate, and combinations thereof, and wherein an amount of the plurality of cellulosic fibers is in a range of from about 5 wt % to about 50 wt % of the substrate and an amount of the plurality of the second fibers in an amount in a range of from about 50 wt % to about 95 wt % of the substrate. In one or more embodiments pertinent to one or more aspects of the present disclosure, the substrate consists essentially of cellulosic fibers. In one or more further embodiments pertinent to one or more aspects of the present disclosure, the substrate consists essentially of cellulosic fibers and polyester; the oil emulsion consists essentially of petrolatum in a range of from about 75 wt % to about 90 wt % of the oil emulsion, mineral oil in a range of from about 10 wt % to about 20 wt % of the oil emulsion, and water in a range of from about 0.1 wt % to about 1 wt % of the oil emulsion; the surfactant consists essentially of sorbitan sesquioleate in a range of from about 1 wt % to about 5 wt % of the oil emulsion; and the at least one antimicrobial agent consists essentially of a biguanide in a range of from about 500 ppm to less than about 1,500 ppm on the substrate but in some cases, the at least one antimicrobial agent consists essentially of a biguanide in a range of from about 1,500 ppm to about 3,500 ppm on the substrate.

One or more aspects of the present disclosure can be directed to a method of preparing a wound dressing. The method can involve providing a substrate comprising polymeric fibers; applying at least one antimicrobial agent on the substrate; and introducing an oil emulsion to the substrate to produce the wound dressing, wherein the oil emulsion consists essentially of petrolatum in a range of from about 75 wt % to about 90 wt % of the oil emulsion, mineral oil in a range of from about 10 wt % to about 20 wt % of the oil emulsion, water in a range of from about 0.1 wt % to about 1 wt % of the oil emulsion, and a surfactant in a range of from about 1 wt % to about 5 wt % of the oil emulsion. In one or more embodiments pertinent to one or more aspects of the present disclosure, providing the substrate comprises preparing a substrate consisting essentially of cellulosic fiber and polyester, and wherein introducing the oil emulsion comprises impregnating the oil emulsion into the substrate in an amount of from about 5 wt % to about 75 wt % of the wound dressing. In one or more embodiments pertinent to one or more aspects of the present disclosure, applying the at least one antimicrobial agent comprises exposing the substrate to a solution comprising polyhexamethylene biguanide to provide from about 500 ppm to about less than 1,500 ppm of the at least one antimicrobial agent on the substrate. In one or more embodiments of the present disclosure, applying the at least one antimicrobial agent comprises exposing the substrate to a solution comprising polyhexamethylene biguanide to provide from about 1,500 ppm to about 3,500 ppm of the at least one antimicrobial agent on the substrate. In one or more embodiments of the present disclosure, the method can further comprise sterilizing the wound dressing.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION

Figure 1:
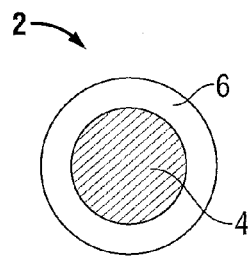
FIGS. 1-5 are schematic illustrations showing cross-sectional views of embodiments of bi-component fibers of a wound dressing, in accordance with one or more aspects of the present disclosure.

One or more embodiments of wound dressings according to the present disclosure may be used in treating burn wounds and other wounds where non-adherent properties of the wound dressing are desirable. The wound dressings typically have enhanced non-adherent properties due to both the inclusion of an oil emulsion and non-adherent polymer materials.

Suitable materials from which the wound dressing may be formed may have the following characteristics: sufficiently strong to avoid tearing of portions thereof; sufficiently inert to avoid foreign body reactions when retained on or in the body for long periods of time; easily sterilized to prevent the introduction of infection when the dressing is placed upon or in the body; and suitable handling characteristics for placement in the desired location on the body. The wound dressing may also be sufficiently pliable to conform to a tissue surface, such as a wound, and flex with movement of the tissue.

One or more aspects of the present disclosure can be directed to advantageously providing a wound dressing with customized properties, such as, for example, any one or more of increased strength, lower surface lint, lower adhesion to a wound, and increased fluid (exudates) transfer, to facilitate wound healing. In some cases, one or more wound dressings of the present disclosure can relate to a wound dressing consisting essentially of a fibrous substrate, a hydrophobic oil emulsion, and a hydrophilic antimicrobial agent. Thus, in some cases, one or more aspects of the present disclosure can be directed to utilizing or incorporating in a wound dressing, at least one antimicrobial agent, such as polyhexamethylene biguanide, that is incompatible in an oil emulsion matrix. One or more further aspects of the present disclosure can pertain to a wound dressing comprising fibers and one or more antimicrobial agents that do not ionically or covalently bind to the surface of the fibers. One or more further aspects of the present disclosure can pertain to wound dressings having one or more antimicrobial agents disposed in a substrate thereof, and further having one or more barriers that controllably regulates the release, diffusion, or elution of the one or more antimicrobial agents from the substrate. For example, the wound dressing can consist essentially of a substrate of cellulosic fibers, an antimicrobial agent in the substrate, and an oil emulsion about the substrate in sufficient amounts to form a barrier that inhibits migration of the antimicrobial agent.

One or more aspects of the disclosure can be directed to wound dressings and methods for making the same. The wound dressing can comprise a substrate having a plurality of yarns and an oil emulsion disposed on the substrate. In some cases, the wound dressing can further comprise at least one antimicrobial agent. In accordance with one or more aspects of the disclosure, the wound dressing can consist essentially of a substrate, an oil emulsion, and an antimicrobial agent. In some cases, the wound dressing can consist essentially of a substrate, an oil emulsion, and an antimicrobial agent. One of the substrate and the oil emulsion may have the at least one antimicrobial or antibacterial agents. In some cases, a wound dressing of the present disclosure can comprise a substrate having a plurality of first yarns comprised of a cellulosic material, a plurality of second yarns fabricated from a non-adherent polymer material, and an oil emulsion disposed on and/or within the substrate.

The substrate, in some embodiments of the disclosure, can be a woven fabric comprising first yarns and second yarns respectively interwoven in a warp direction and in a weft direction. In other cases, the substrate can be a woven fabric comprising first yarns and second yarns respectively interwoven in a weft direction and in a warp direction. In some cases, the substrate can comprise a plurality of first yarns comprising cellulosic fibers. In some cases, the substrate can consist of cellulosic fibers. In still other cases, the substrate can further comprise a plurality of second yarns comprising non-adherent polymeric fibers. In accordance with some embodiments of the disclosure, the first yarns can comprise at least one of a bast fiber and another cellulosic fiber, and the second yarns can comprise non-adherent polymeric fibers. In still other cases, the substrate can consist of or consist essentially of cellulosic fibers and a non-adherent polymeric fibers. In yet other cases, the substrate can consist of or consist essentially of bast fibers and cellulosic acetate fibers. For example, the wound dressing can comprise a substrate that consists of first yarns of at least one of a bast fiber and a cellulosic fiber, and second yarns of non-adherent polymeric fibers; and an oil emulsion disposed on at least a portion the substrate. In accordance with still further embodiments of the disclosure, the wound dressing can consist essentially of first yarns consisting essentially of at least one of a bast fiber and a cellulosic fiber, and second yarns consisting essentially of non-adherent polymeric fibers; and an oil emulsion disposed on at least a portion the substrate. In accordance with yet further embodiments of the disclosure, the wound dressing can consist of first yarns consisting of at least one of a bast fiber and a cellulosic fiber, and second yarns consisting of non-adherent polymeric fibers; and an oil emulsion disposed on at least a portion the substrate. One or more aspects of the disclosure can be directed to a wound dressing consisting essentially of a substrate of cellulose acetate yarns with excess oil emulsion to saturate the substrate. One or more aspects of the disclosure can be directed to a wound dressing consisting essentially of a knitted substrate of cellulose acetate yarns and from about 5 wt % to about 75 wt % of an oil emulsion. One or more aspects of the disclosure can be directed to a wound dressing consisting of a knitted substrate of polyester yarn and from about 5 wt % to about 75 wt % of oil emulsion. One or more aspects of the disclosure can be directed to a wound dressing consisting essentially of a knitted substrate of polyester yarn and from about 5 wt % to about 75 wt % of oil emulsion. One or more aspects of the disclosure can be directed to a wound dressing consisting of a knitted substrate of polyester yarn and from about 5 wt % to about 75 wt % of oil emulsion.

The first yarns, in some embodiments of the disclosure, can be heterogeneous yarns comprising a first cellulosic fiber and a second cellulosic fiber. The first yarns, in some embodiments of the disclosure, can be heterogeneous yarns consisting essentially of a first cellulosic fiber and a second cellulosic fiber. The heterogeneous yarns, in some embodiments of the disclosure, can consist of a first cellulosic fiber and a second cellulosic fiber. The first yarns, in some embodiments of the disclosure, can comprise heterogeneous yarns comprising a cellulosic material and a bast fiber. The first yarns, in some embodiments of the disclosure, can consist essentially of a cellulosic fiber and a bast fiber. The first yarns, in some embodiments of the disclosure, can consist of a cellulosic fiber and a bast fiber. The first yarns, in accordance with some embodiments of the disclosure, can consist essentially of bast fibers. In accordance with further embodiments of the disclosure, the first yarns can consist of bast fibers. The first yarns, in some embodiments of the disclosure, can comprise at least one of cotton and viscose rayon.

In some embodiments of the disclosure, at least a portion of the plurality of second yarns can be comprised of a non-adherent polymeric material selected from the group consisting of polyethylene, polypropylene, polyfluoroethylene, polyfluoropropylene, polyfluoropolyethylene glycol, polytetrafluoroethylene, polyethylene terephthalate, polyethylene naphthalate, polytrimethylene terephthalate, polybutylene terephthalate, and combinations thereof. The cellulosic material, in some embodiments of the disclosure, can comprise about 5% to about 50% by weight of the substrate. The non-adherent polymeric fibers, in some embodiments of the disclosure, can comprise about 50% to about 95% by weight of the substrate. The wound dressing, in accordance with one or more embodiments of the disclosure, can further comprise at least one bacteriostatic agent, such as with the oil emulsion. The at least one bacteriostatic agent can be bismuth tribromophenate. The wound dressing, in accordance with one or more embodiments of the disclosure, can further comprise at least one antimicrobial agent, such as with the oil emulsion. The at least one antimicrobial agent can be polyhexamethylene biguanide (PHMB).

The at least one antimicrobial agent can include, for example, biguanides such as but not limited to polyhexamethylene biguanide. The at least one antimicrobial agent may be present in an amount in a range of from about 500 ppm to about 3,500 ppm and in some cases in a range of from about 1,500 ppm to about 3,500 ppm. In some particular cases, the at least one antimicrobial agent is present in the substrate in a range of from about 500 ppm to about 1,000 ppm.

The at least one antimicrobial agent may be applied directly to the substrate either before or after application of the oil emulsion. The one or more antimicrobial agent may be applied using any suitable method within the purview of those skilled in the art including, but not limited to, spraying, solution casting, dipping, and combinations thereof. For example, U.S. Pat. No. 6,349,289 titled "Method and Manufacture of a Wound Dressing for Covering an Open Wound" describes a system and method for applying PHMB to a cellulosic bandage, which is incorporated by reference herein for all purposes.

The oil emulsion can include soft paraffin, which is a semi-solid mixture at room temperature, of hydrocarbons with a carbon number of at least about twenty-five. The oil emulsion can comprise petrolatum, and can denote a composition including a mixture of hydrocarbons having a Chemical Abstracts Service Registry No. 8009-03-8. Oil emulsions that can be utilized in accordance in one or more of the configurations disclosed herein can comprise petrolatum, water, and at least one surfactant. In some configurations, the oil emulsion can further comprise a mineral oil. The oil emulsion can comprise a petrolatum in a range of from about 75 wt % to about 90 wt % of the oil emulsion, a mineral oil in a range of from about 10 wt % to about 20 wt % of the oil emulsion, water in a range of from about 0.1 wt % to about 1 wt % of the oil emulsion, and at least one surfactant in a range of from about 1 wt % to about 5 wt % of the oil emulsion. In other configurations, the oil emulsion can consist essentially of a petrolatum, a mineral oil, water, and a surfactant. In some cases, the oil emulsion can consist of a petrolatum in a range of from about 75 wt % to about 90 wt % of the oil emulsion, a mineral oil in a range of from about 10 wt % to about 20 wt % of the oil emulsion, water in a range of from about 0.1 wt % to about 1 wt % of the oil emulsion, and at least one surfactant. In some particular configurations, the oil emulsion can consist essentially of about 81 wt % petrolatum, about 0.5 wt % water, about 16.5 wt % mineral oil, and about 2 wt % sorbitan sesquioleate.

The mineral oil can be or can comprise light mineral oil, such as but not limited to DRAKEOL™ 7 mineral oil, available from, for example, Calumet Specialty Products Partners, L.P., Indianapolis, Ind.

The one or more surfactants that may be utilized in one or more embodiments may be selected from nonionic surfactants and ionic surfactants such as anionic surfactants, cationic surfactants, and zwitterionic surfactants. The at least one surfactant may be added as a solid or as a solution with a concentration in a range of from about 5% to about 100% (pure surfactant) by weight of the solution. The at least one surfactant may be utilized so that it is present in an amount in a range of from about 0.01 weight percent to about 20 weight percent of the oil emulsion. In some cases, the concentration of the at least one surfactant may be in a range of from about 0.1 weight percent to about 16 weight percent of the oil emulsion. In some cases, the concentration of the at least one surfactant may be in a range of from about 1 wt % to about 5 wt % of the oil emulsion.

Anionic surfactants which may be utilized include but are not limited to sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid available from Aldrich, NEOGEN R™, NEOGEN SC™ available from Daiichi Kogyo Seiyaku (Japan), DOWFAX™ 2A1, an alkyldiphenyloxide disulfonate available from The Dow Chemical Company, Midland, Mich., and TAYCA POWER BN2060 available from Tayca Corporation, Japan, which are branched sodium dodecylbenzene sulfonates. Combinations of any one or more of these surfactants may be utilized.

Non-limiting examples of the cationic surfactants include, for example, alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quaternized polyoxyethylalkylamines, dodecylbenzyl triethyl ammonium chloride, MIRAPOL™ and ALKAQUAT™, available from Alkaril Chemical Company, and benzalkonium chloride such as SANIZOL™, available from Kao Chemicals, and mixtures thereof.

Non-limiting examples of nonionic surfactants that may be utilized include, for example, polyacrylic acid, methalose, methyl cellulose, ethyl cellulose, propyl cellulose, hydroxyethyl cellulose, carboxymethyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, sorbitan sesquioleate, polyoxyethylene stearyl ether, polyoxyethylene nonylphenyl ether, dialkylphenoxy poly(ethyleneoxy)ethanol, available from Rhone-Poulenc as IGEPAL CA-210™, IGEPAL CA-520™, IGEPAL CA-720™, IGEPAL CO-890™, IGEPAL CO-720™, IGEPAL CO-290™, IGEPAL CA-210™, ANTAROX890™ and ANTAROX897™, block copolymers of polyethylene oxide and polypropylene oxide, including those commercially available as SYNPERONIC PE/F, and SYNPERONIC PE/F 108. Combinations of these surfactants and any one or more of the foregoing surfactants may be utilized.

One or more aspects of the disclosure can be directed to a wound dressing comprising an antimicrobial agent, a knitted substrate comprising a polyester yarn having the antimicrobial agent; and an oil emulsion disposed on at least a portion of the knitted substrate. In accordance with some embodiments of the disclosure, the wound dressing can comprise an antimicrobial agent, a knitted substrate consisting essentially of a polyester yarn, and an oil emulsion disposed on the knitted substrate. In accordance with some embodiments of the disclosure, the wound dressing can comprise an antimicrobial agent, a knitted substrate consisting of a polyester yarn, and an oil emulsion disposed on at least a portion of the knitted substrate. In some embodiments of the disclosure, the substrate can comprise a weft knitted fabric with from about 5 wt % to about 75 wt % of oil emulsion. In some embodiments of the disclosure, the substrate comprises a warp knitted fabric with from about 5 wt % to about 75 wt % of oil emulsion. The wound dressing, in accordance with some embodiments of the disclosure, can comprise from about 1 wt % to about 5 wt % of at least one of an antimicrobial agent and a bacteriostatic agent.

One or more aspects of the disclosure can be directed to a wound dressing comprising a substrate comprised of a polymer that is non-adherent to wound surfaces; and an oil emulsion impregnated into at least a portion of the substrate. One or more further aspects of the disclosure can be directed to a wound dressing consisting essentially of a substrate of a polymer that is non-adherent to wound surfaces; and an oil emulsion impregnated into at least a portion of the substrate. One or more still further aspects of the disclosure can be directed to a wound dressing consisting of a substrate of a polymer that is non-adherent to wound surfaces; and an oil emulsion impregnated into at least a portion of the substrate. The substrate, in accordance with some embodiments of the disclosure, can consist essentially of woven polyester fibers or yarns with from about 5% to about 75% oil emulsion, by weight of the wound dressing. The substrate, in accordance with further embodiments of the disclosure, can consist essentially of nonwoven polyester fibers or yarns with from about 5% to about 75% oil emulsion, by weight of the wound dressing. The non-adherent polymer can be a material selected from the group consisting of polyethylene, polypropylene, polyfluoroethylene, polyfluoropropylene, polyfluoropolyethylene glycol, polytetrafluoroethylene, polyethylene terephthalate, polyethylene naphthalate, polytrimethylene terephthalate, and polybutylene terephthalate. In particular embodiments of the disclosure, the substrate consists of a combination of two or more of the non-adherent polymers.

In one or more aspects of the disclosure, preparing a wound dressing can comprise providing a fabric comprising cellulosic fibers woven with non-adherent polymeric fibers comprised of at least one polymer selected from the group consisting of polyester, polypropylene, polyethylene, and polytetrafluoroethylene; and impregnating an oil emulsion into the fabric to produce the wound dressing; and sterilizing the wound dressing. In some embodiments of the disclosure, providing the fabric comprises weaving the non-adherent polymeric fibers, in a warp direction, with the cellulosic fibers, in the weft direction, to produce a woven fabric with at least about 50% by weight of non-adherent polymeric fibers. In some further embodiments of the disclosure, providing the fabric comprises weaving the cellulosic fibers, in a warp direction, with the non-adherent polymeric fibers, in the weft direction, to produce a woven fabric with at least about 50% by weight of non-adherent polymeric fibers. In still further embodiments of the disclosure, providing the fabric comprises weaving at least a portion of the non-adherent polymeric fibers with at least a portion of the cellulosic fibers in the warp direction to produce a woven fabric with at least about 50% by weight of non-adherent polymeric fibers. In yet further embodiments of the disclosure, providing the fabric comprises weaving at least a portion of the non-adherent polymeric fibers and at least a portion of the cellulosic fibers in the weft direction to produce a woven fabric with at least about 50% by weight of non-adherent polymeric fibers. One or more embodiments of the disclosure can further comprise disposing the fabric into a sealable package, and wherein impregnating the oil emulsion comprises introducing oil emulsion into the fabric that is disposed in the sealable package. In some embodiments of the disclosure, providing the fabric can comprise weaving the at least one of cellulosic fibers and bast fibers with the non-adherent polymeric fibers to produce a woven article; bleaching the woven article; tentering the bleached, woven article; cutting the bleached, woven article to produce a woven fabric; folding the woven fabric to produce a gauze. In some further embodiments of the disclosure, folding the woven fabric comprises folding the woven fabric to produce the gauze having any of three plies, four plies, five plies, six plies, eight plies, ten plies, twelve plies, sixteen plies, 24 plies, 32 plies, 48 plies, 50 plies, 144 plies, and 216 plies. One or more embodiments of the disclosure can further comprise introducing at least one bacteriostatic agent into the fabric. One or more embodiments of the disclosure can further comprise introducing at least one antimicrobial agent into the fabric. In some embodiments of the disclosure, the non-adherent polymeric fiber can be comprised of a material selected from the group consisting of polyethylene, polypropylene, polyfluoroethylene, polyfluoropropylene, polytetrafluoroethylene, polyethylene terephthalate, polyethylene naphthalate, polytrimethylene terephthalate, polybutylene terephthalate, and combinations thereof. In accordance with one or more aspects of the disclosure, facilitating wound treatment can comprise providing a fabric comprising cellulosic fibers woven with non-adherent polymeric fibers comprised of at least one polymer selected from the group consisting of polyester, polypropylene, polyethylene, and polytetrafluoroethylene; and impregnating an oil emulsion into the fabric to produce the wound dressing; and sterilizing the wound dressing.

The first yarns can comprise, but are not limited to, naturally occurring cellulosic materials as well as synthetically-modified and/or regenerated cellulose materials. Synthetically-modified and/or regenerated cellulosic materials include cellulose and polysaccharide derivatives, including alkyl celluloses, hydroxyalkyl celluloses, cellulose ethers, cellulose esters, nitrocelluloses, and chitosan. Specific examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses." Additional synthetic cellulosic materials include, but are not limited to, rayon, rayon acetate, viscose rayon, and lyocell. Natural cellulosic materials that may be utilized in any one or more configurations of the disclosure include, for example, cotton, linen, combinations, and derivatives thereof. Other materials that may be utilized in any one or more configurations of the disclosure include, for example, bast fibers or other fibers derived from plant stems or barks such as, for example, flax, hemp, jute, ramie, and derivatives thereof. Other materials can include manmade cellulosic materials such as, for example, rayon, rayon acetate, viscose rayon, lyocell, and combinations thereof. Synthetically modified natural polymers of cellulose derivatives may be utilized in any one or more configurations of the disclosure include, for example, alkyl celluloses, hydroxyalkyl celluloses, cellulose ethers, cellulose esters, nitrocelluloses, and chitosan. Non-limiting examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. Any of the substrates can incorporate one or more types of fibers. For example, one or more embodiments of the disclosure can comprise any of cotton, linen, with any one or more bast fibers such as any of flax, hemp, jute, and ramie. Commercially available bast fibers that can be utilized in the various embodiments of the disclosure include those available as, for example, CRAILAR fibers from Naturally Advanced Technologies Inc., Victoria, British Columbia, Canada.

Suitable non-adherent polymeric materials that can be utilized in any of the substrates disclosed herein can include, but are not limited to, polyolefins such as polyethylene and polypropylene including atactic, isotactic, syndiotactic, and blends thereof; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides such as nylon and polycaprolactam; polyamines; polyimines; polyesters such as polyethylene terephthalate, polyethylene naphthalate, polytrimethylene terephthalate, and polybutylene terephthalate; polyethers; polybutylester; polytetramethylene ether glycol; 1,4-butanediol; polyurethanes; acrylic polymers; methacrylics; polychlorofluoroethylene; polyacrylonitrile; polyaryletherketones; polyvinyl ketones; copolymers of vinyl monomers with each other and olefins; acrylonitrile-styrene copolymers; polyimides; aramids; rayon; rayon-triacetate; and copolymers and combinations thereof. In other cases, the non-adherent fibers that can be utilized in any of the substrates disclosed herein can be comprised of sodium alginate, calcium alginate, or combinations thereof.

Thus, for example, some aspects of the present disclosure can be directed to embodiments of wound dressings comprising at least one woven, nonwoven, or knitted substrate of alginate fibers and petrolatum. In other embodiments, however, the wound dressing can consist essentially of any of a woven substrate of alginate fibers, a nonwoven substrate of alginate fibers, and a knitted substrate of alginate fibers; and petrolatum. In other embodiments, however, the wound dressing can consist of any of a woven substrate of alginate fibers, a nonwoven substrate of alginate fibers, and a knitted substrate of alginate fibers; and petrolatum.

The wound dressing can comprise bi-component, monofilament, or multifilament fibers formed from cellulosic and/or non-adherent polymeric materials. Bi-component fibers are typically fibers of two polymers which may have different chemical and/or physical properties. Bi-component fibers may include cellulosic material in a range of from 5% to about 50% by weight of the fibers, in some cases, in a range of from about 10% to about 45% by weight of the fibers, and in accordance with some further embodiments of the disclosure, in a range of from about 15% to about 40% by weight of the fibers. The bi-component fibers may include any of the non-adherent polymeric material described herein in an amount of from 50% to about 95% by weight of the fiber, in some cases, in a range of from about 55% to about 90% by weight of the fiber, and in further embodiments, in a range of from about 60% to about 80% by weight of the fibers. As exemplarily illustrated in FIG. 1, bi-component fiber 2 can have a core polymer 4 and a sheath polymer 6. Core polymer 4 may be fabricated from a first polymeric material and sheath polymer 6 may be fabricated from a second polymeric material having different characteristics than the first polymeric material.

Figure 2:
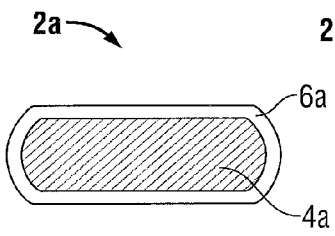
Figure 3:
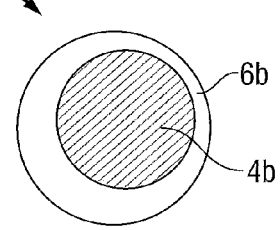
Figure 4:
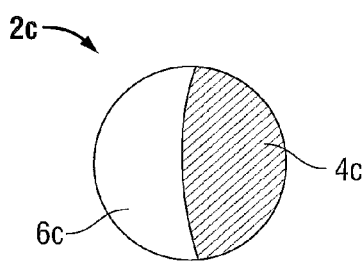

Bi-component fiber 2 may be a monofilament fiber which is, for example, coextruded from two distinct polymers to exhibit a concentric sheath-core arrangement. Fiber 2 can have a round cross-sectional profile including a core polymer 4 surrounded by a sheath polymer 6. The core polymer 4 and sheath polymer 6 can be concentrically arranged. In any one or more configuration of the various fibers may involve various cross-sectional shapes, such as a flattened cross-sectional shape as exemplarily illustrated by fiber 2a in FIG. 2, which includes a core polymer 4a and a sheath polymer 6a, as well as other modified cross-sections configurations which may be co-extruded to generate fibers with more complex profiles. As illustrated in FIG. 3, bi-component fiber 2b may also exhibit an eccentric (e.g., offset center) sheath-core arrangement. Fiber 2b can have an off-center core polymer 4b surrounded by sheath polymer 6b. FIG. 4 illustrates a bi-component fiber 2c similar to fibers 2, 2a, 2b, but differs in that core polymer 4c and sheath polymer 6c each can occupy a portion of the outer surface of the fiber 2c.

Figure 5:
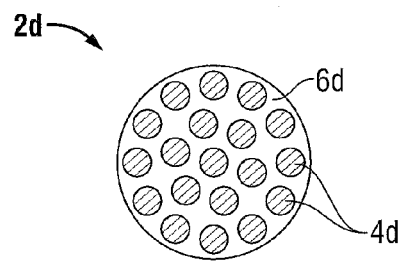

As exemplarily illustrated in FIG. 5, bi-component fiber 2d may also be a multifilament fiber which may be spun and processed from microdenier filaments of core polymer 4d. Fiber 2d can exhibits an islands-in-the-sea arrangement where two or more "islands," or core polymer filaments 4d are surrounded by a "sea," or sheath polymer 6d. This arrangement may provide for very fine strands of island polymer filaments 4d to be effectively handled by manufacturing equipment to spin and form fiber 2d. Core polymer filaments 4d may be arranged so as to be generally non-intersecting along their length. Although not necessarily parallel, core polymer filaments 4d may be generally free from entanglement or interlacing over a substantial portion of their length.

Alternatively, core polymer filaments 4d may be woven, braided, or entangled by various processes within the purview of those skilled in the art. The core polymer filaments 4d may be spun inside the sheath polymer 6d. The number of polymer filaments 4d formed within the fiber 2d may be from about two to about fifty, in embodiments may be from about ten to about forty.

The sheath polymer may be applied to the core polymer of the bi-component fiber by, for example, extrusion, co-extrusion, pultrusion, gel spinning with one of the aforementioned processes, melt coating, spray coating, ultrasonic spray coating, electrostatic coating, powder coating, solvent/immersion coating such as dipping, spraying, solvent evaporation, sheath heat crimping, chemical surface modification, and combinations thereof.

The surface of the core polymer may be porous to facilitate anchoring or impregnating at least a portion of the sheath polymer into the core. Any of the fibers can have a tailored or predetermined porosity which may be achieved by roughening the surface of the core polymer. Alternatively, the core polymer may have a smooth, non-porous surface such that the core and sheath polymers have little or no adhesion to each other.

In accordance with some embodiments of the disclosure, the core of the bi-component fiber can provide strength and maintain the integrity of the entire bi-component fiber, while the sheath can provide a smooth, non-adherent outer surface which can be advantageous in promoting non-adherence when displaced against tissue.

Figure 7:
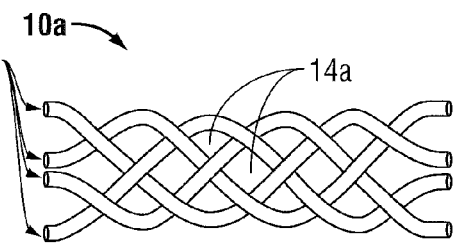
FIG. 7 is schematic illustration showing a perspective view of an embodiment of a yarn of a wound dressing, in accordance with one or more aspects of the present disclosure.
Figure 8:
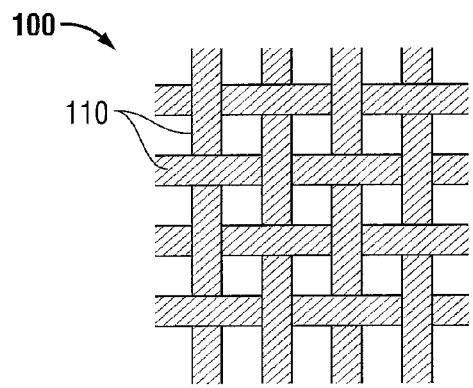
FIGS. 8-16 are schematic illustrations of various embodiments, in accordance with one or more aspects of the present disclosure.

FIGS. 7 and 8 exemplarily illustrate embodiments in accordance with some aspects the disclosure that utilize multifilament yarns. Two or more filaments may be used to form the multifilament yarns. The filament may be arranged to create openings therebetween and the yarns may also be arranged relative to each other to form openings in the wound dressing. The spacing between the yarns may vary depending on the medical or surgical application and desired wound dressing properties. Any of the wound dressings in accordance with any one or more aspects of the disclosure may be of any suitable size.

Figure 6:
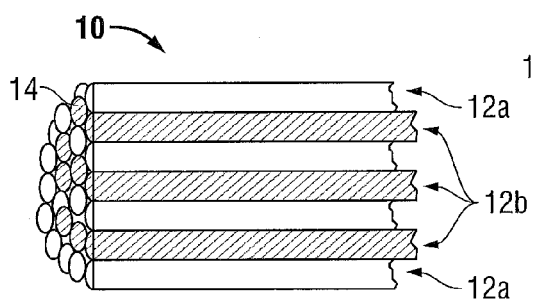
FIG. 6 is schematic illustration showing a perspective view in partial cross-section of an embodiment of a yarn of a wound dressing, in accordance with one or more aspects of the present disclosure.

Multifilament yarns may be heterogeneous or homogeneous yarns. As illustrated in FIG. 6, heterogeneous yarns 10 can be configured to include at least two dissimilar filaments 12a and 12b and include openings 14 formed between filaments 12a and 12b. Yarns 10, such as, filaments 12a and 12b, may be formed from cellulosic and non-adherent polymeric materials.

Homogeneous yarns 10a, as shown in FIG. 7, can be configured to include at least two substantially similar filaments 12a, and can also include openings 14a formed between filaments 12a. In embodiments in which at least two filaments form a yarn, the filaments may be drawn (FIG. 6), braided (FIG. 7), or otherwise oriented, crinkled, twisted, commingled or air entangled to form the yarn.

Yarns may include any number of fibers and be dimensioned in a variety of sizes and shapes. Yarns may have a size ranging from about 25 English cotton yarn number (Ne) count to about 40 Ne count, in embodiments from about 30 Ne to about 37 Ne. Yarns may have a break factor from about 1,700 pound cotton count (lb·Ne) to about 2,500 lb·Ne, in embodiments from about 2,000 lb·Ne to about 2,200 lb·Ne.

The yarns may be braided, twisted, aligned, fused, or otherwise joined to form a variety of different wound dressing configurations. The yarns may be woven, knitted, interlaced, braided, or combinations thereof, to be formed into a substrate, such as a fabric, for a wound dressing or by other non-weaving techniques. The structure thereof will vary depending upon the assembling technique utilized to form the fabric, as well as other factors such as the type of fibers used, the tension at which the yarns are held, and the mechanical properties required of the wound dressing.

In some embodiments in accordance with some aspects of the disclosure, knitting may be utilized to form any of the various wound dressings. Knitting typically involves the intermeshing of yarns to form loops, or interloping of the yarns. In some embodiments of the disclosure, any of the various herein disclosed yarns may be warp-knitted thereby creating vertical interlocking loop chains and/or may be weft-knitted hereby creating rows of interlocking loop stitches across the wound dressing.

Any of the substrates of the present disclosure may be formed into a nonwoven substrate by any technique including any of mechanically, chemically, thermally bonding the yarns into a sheet or web in a random or systematic arrangement. For example, one or more yarns of the present disclosure may be mechanically bound by entangling the yarns to form the wound dressing by means other than knitting or weaving, such as matting, pressing, stitch-bonding, needlepunching, or otherwise interlocking the yarns to form a binderless network. Alternatively, any of the yarns may be chemically bound by an adhesive, such as a hot melt adhesive, or be thermally bound by a binder such as a powder, paste, or melt, and melting the binder on the sheet or web of yarns.

In other cases, any of the substrates of the present disclosure may be formed by spunlacing or hydroentangling fiber or yarns that have been formed by carding, airlaying, or wet-forming processes, and striking the yarns or fibers with high speed jets of water to at least partially entangle at least a portion of the yarn or fiber, with itself and/or with other yarns or fibers. In still other cases, any of the nonwoven substrates of the present disclosure may be formed by needlepunching a precursor web of fibers or yarns, which typically have been prepared by spunbonding or by carding, and striking the yarns or fibers with barbed felting needles to at least partially interlock at least a portion of the yarn or fiber, with itself and/or with other yarns or fibers. In yet other cases, any of the nonwoven substrates of the present disclosure may be formed by extruding molten polymeric material into filaments, overlaying the molten filaments and allowing the filaments to cool and form bonds at contact points. In further cases, any of the substrates of the disclosure can be formed by meltblowing techniques which typically involve extruding molten polymeric material and drawing the extruded molten filaments with high velocity jets of air to form fine filaments that have one or more bond contact points. In yet further cases, any of the substrates of the disclosure may be formed by preparing a precursor web with thermoplastic polymeric material, which typically can be formed by any of carding, airlaying, or spunbonding, and melting at least a portion of the thermoplastic material, typically by utilizing heated calender rolls, to form bonds with other fibers. In yet further cases, any of the substrates of the present disclosure can be formed by chemically bonding at least a portion of fibers in the substrate by utilizing a chemical binder, such as latex.

Weaving may be utilized to form any of the substrates or wound dressings of the disclosure. Weaving may involve, for example, the intersection of two sets of straight yarns, warp and weft, which cross and interweave at right angles to each other, or the interlacing of two yarns at right angles to each other. The yarns may be arranged to form a net wound dressing which has isotropic or near isotropic tensile strength and elasticity.

Yarns described above may include any number and combination of multifilament, monofilament, and/or bi-components fibers formed from cellulosic or non-adherent polymeric materials. Cellulosic material may be present in an amount from 5% to about 50% by weight of the yarns, in embodiments from about 10% to about 45% by weight of the yarns, and in further embodiments from about 15% to about 40% by weight of the yarns. The yarns may include the non-adherent polymeric material described above from 50% to about 95% by weight of the yarns, in embodiments from about 55% to about 90% by weight of the fiber, and in further embodiments from about 60% to about 80% by weight of the yarns.

As illustrated in FIG. 8, substrate or wound dressing 100 can include yarns 110 including fibers of cellulosic and non-adherent polymeric materials. Yarns 110 may be monofilament or multifilament, homogeneous or heterogeneous yarns, as described herein. While illustrated as being woven, the yarns 110 may be interconnected in any manner as described herein. For example, yarns in staple form may be spun using standard spinning methodologies, such as open end spinning, ring spinning, air jet spinning, and other techniques to form any of the substrates.

Figure 9:
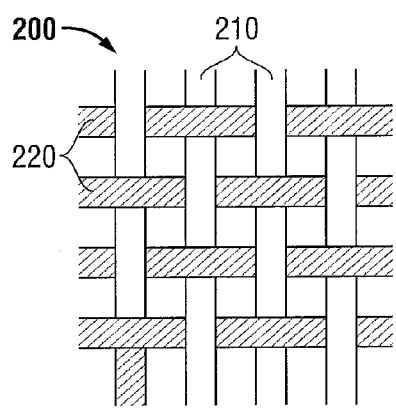
Figure 10:
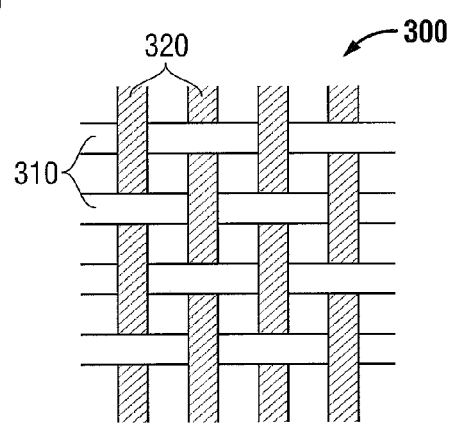

As shown in FIG. 9, substrate or wound dressing 200 can include first yarns 210 including cellulosic fibers arranged in a warp direction and second yarns 220 including non-adherent polymeric fibers interlaced between the first yarns 210 in a weft direction to form a weaved pattern. In a further embodiment, as shown in FIG. 10, substrate or wound dressing 300 may include first yarns 310 including cellulosic fibers arranged in a weft direction and second yarns 320 including non-adherent polymeric fibers in a warp direction.

Figure 11:
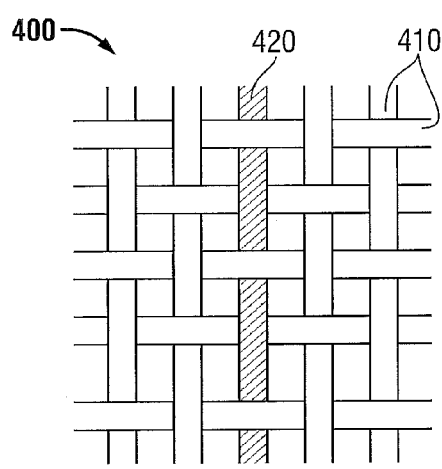
Figure 12:
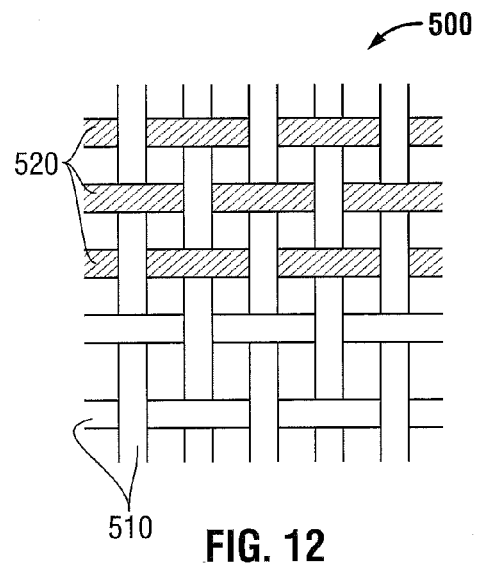
Figure 13:
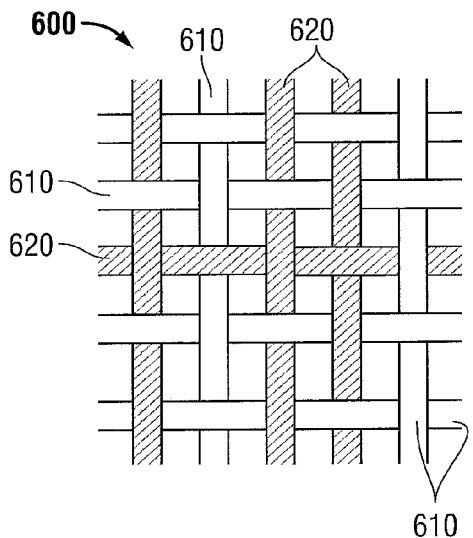

In other embodiments, as illustrated in FIG. 11-13, any of substrates or wound dressings 400, 500, and 600 may include at least one yarn 420 including non-adherent polymeric fibers in a warp direction (FIG. 11), at least one yarn 520 including non-adherent polymeric fibers in a weft direction (FIG. 12), or at least one yarn 620 including non-adherent polymeric fibers in both warp and weft directions (FIG. 13). The remainder of the yarns 410, 510, and 610 include cellulosic fibers.

Figure 14:
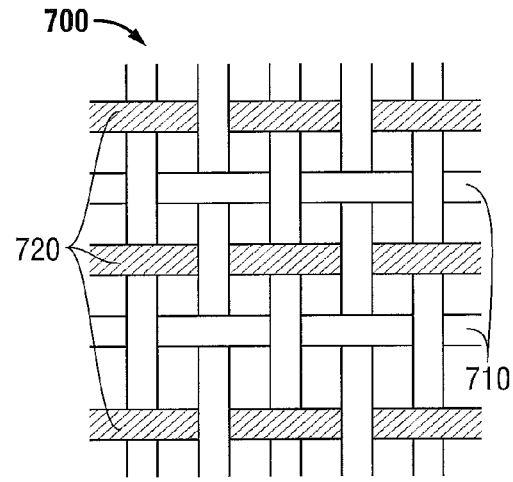
Figure 15:
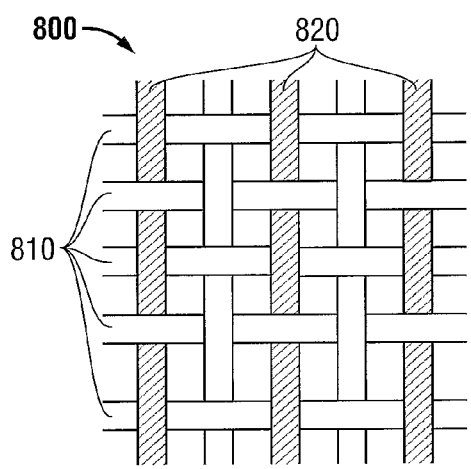
Figure 16:
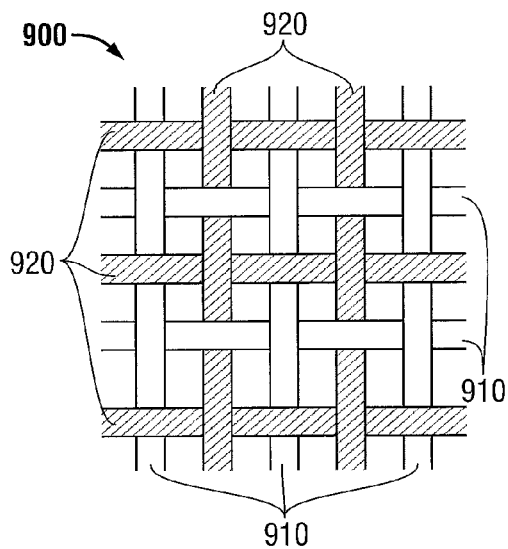

FIG. 14-16 illustrate substrates or wound dressings 700, 800, and 900 including alternating yarns of cellulosic and polymer fibers. As shown in FIG. 14, yarns 710 can comprise cellulosic fibers and yarns 720 can comprise non-adherent polymeric fibers alternate in a weft direction, with fibers 710 including cellulosic fibers making up the yarns in the warp direction. FIG. 15 illustrates yarns 810 including cellulosic fibers and yarns 820 including non-adherent polymeric fibers alternating in a warp direction, with yarns 810 including cellulosic fibers making up the yarns in the weft direction. FIG. 16 illustrates yarns 910 including cellulosic fibers and yarns 920 including polymer fibers alternating in both warp and weft directions.

Wound dressings may include any number and combination of yarns formed from multifilament, monofilament, and/or bi-component fibers, which are formed from cellulosic or non-adherent polymeric materials. Cellulosic material may be present in an amount from 5% to about 50% by weight of the wound dressings, in embodiments from about 10% to about 45% by weight of the wound dressings, and in further embodiments from about 15% to about 40% by weight of the wound dressings. The wound dressings may include the non-adherent polymeric material described above from 50% to about 95% by weight of the wound dressings, in embodiments from about 55% to about 90% by weight of the fiber, and in further embodiments from about 60% to about 80% by weight of the wound dressings. In further embodiments, the wound dressing according to the present disclosure about 50% or more by weight of non-adherent polymeric fibers.

The fabric for fabricating the dressing, once formed, e.g., by weaving or knitting, may be bleached and may optionally be sterilized. Thereafter, the fabric may be tentered, e.g., setting warp and weft of the fabric at substantially right angles with respect to each other and stretching the yarns. The fabric can then be dried and cut into desired size. The cut portions of the fabric may then be folded to produce the substrate. Particular embodiments of the disclosure can involve embodiments comprising an absorbent gauze comprising cotton, with not more than about 55% by weight of rayon, as a plain woven cloth. Preferably, the absorbent gauze is sterile. Any of the various embodiments of the disclosure can involve substrates, such as an absorbent gauze, comprising warp threads in a range of from about 41 to about 47 per centimeter, filling threads in a range of 33 to 39 per centimeter. Any of the various embodiments of the disclosure can involve substrates, such as an absorbent gauze, with an average thread count in a range of about 76 to about 84 threads per 6.45 cm$^2$, and basis weight in a range of from about 43.8 to about 55.8 grams per square meter. Any of the various embodiments of the disclosure can involve substrates, such as an absorbent gauze, comprising warp threads in a range of from about 18 to about 22 per centimeter, filling threads in a range of 8 to 14 per centimeter. Any of the various embodiments of the disclosure can involve substrates, such as an absorbent gauze, with an average thread count in a range of about 27 to about 35 threads per 30 6.45 cm$^2$, and basis weight in a range of from about 18.1 to about 23.1 grams per square meter. Any of the various embodiments of the disclosure can involve substrates, such as an absorbent gauze, comprising warp threads in a range of from about 12 to about 16 per centimeter, filling threads in a range of 8 to 12 per centimeter. Any of the various embodiments of the disclosure can involve substrates, such as an absorbent gauze, with an average thread count in a range of about 21 to about 27 threads per 6.45 cm$^2$, and basis weight in a range of from about 12.1 to about 15.5 grams per square meter.

It is envisioned that any number of yarns, in various arrangements and patterns, may be used to form the substrates and wound dressings of the present disclosure. The yarns, fabrics, or substrates may be scoured and bleached to meet desirable, suggested, and/or mandated standards, such as the gauze fabric standards from United States Pharmacopeial Convention. The yarns, fabrics, substrates or wound dressings may be sterilized using standard sterility protocols to conform to suggested or mandated sterility standards. For example, the various embodiments or components thereof of the disclosure can be sterilized to conform with sterilization standards of medical devices as set forth by the International Organization for Standardization including, for example, any of ISO 11135 for ethylene oxide sterilization for medical devices, ISO 11137 for gamma and e-beam sterilization for medical devices, and ISO 17665 for steam sterilization for medical devices. Sterilizing any of the yarns, substrates, gauze and wound dressings of the disclosure can involve any suitable technique that provides a desired level of sterility, such as a desired sterility assurance level, including, for example, any one or more of physical processes such as steaming, autoclaving, heating, chemical processes such as exposure to agents such as hydrogen peroxide, ethylene oxide, ozone, silver ions, or other oxidizing compounds such as sodium hypochlorite, irradiation processes such as exposure to gamma rays, electron beams, ultraviolet light and x-ray energy, and combinations thereof.

The fabricated substrate, e.g., gauze, may be impregnated or otherwise treated with an oil emulsion to produce the wound dressing. In accordance with embodiments of the disclosure, petrolatum may be applied to the substrate, such as gauze, after being disposed in a sealable package, e.g., prior to the package is sealed. Petrolatum may thus be selectively disposed on the wound-contacting surface of the wound dressing. In some cases, the oil emulsion may be applied to the entire wound dressing to fully impregnate all layers of the substrate. The amount of the oil emulsion present in the dressing may be from about 5% to about 75% by weight of the wound dressing, in embodiments may be from about 25% to about 50% by weight of the wound dressing. The substrate, or dressing, can then be sterilized, such as by exposure to steam in accordance with ISO 17665. Sterilization can be performed before or after introducing the oil emulsion in the package.

Bioactive agents such as PHMB, bismuth tribromophenate, or other medicaments, antimicrobial agents, bacteriostatic agents, hemostatic agents, tissue scaffolding agents, anti-thrombogenic agents, vasodilation agents, anesthetic agents, anti-inflammatory agents, anticancer agents, angiostatic agents, immune boosting agents, skin sealing agents, wound healing agents, and/or wound debriding agents, may be used to, for example, decrease the incidence of infection or otherwise promote healing of a wound. Other agents include those used in slow release treatments wherein the agent is released from a fiber or yarn into the wound over a period of time. Other bioactive agents that may be utilized in any one or more variant embodiments of the disclosure can include, for example, therapeutic agents, organoleptic agents, and pharmaceutical agents. Any of the one or more bioactive agents may be disposed into any the fibers, yarns, substrates, and wound dressings of the disclosure by immersion thereof in a solution including the one or more agents, and, optionally, drying the solvents from the immersed, coated, infused fiber, yarn, substrate or wound dressing to any desired bioactive agent concentration, for example, to a concentration that at least partially inhibits any microbial activity therein. Introduction of the one or more bioactive agents can be performed during or after any one or more yarns fabrication, substrates fabrication, or wound dressing fabrication, or, in some cases, after any one of bleaching, and sterilizing. Further aspects of the disclosure can be directed to methods or techniques utilizing the substrates and gauze as wound dressings as disclosed herein to absorb wound exudates, to protect wounds, to cushion wound sites. Such methods and techniques can involve securing any of the wound dressings on the wound or wound site, replacing the wound dressing, and/or reapplying the wound dressing comprising, consisting essentially of, or consisting of the first and second fibers. The bioactive agent can be in an amount ranging from about 1 wt % to about 5 wt %, based on the weight of the dressing.

The oil emulsion can be prepared by heating to a temperature sufficient to melt or liquefy the petrolatum, such as to a temperature in a range of from about 38° C. to about 60° C., adding and mixing mineral oil into the melted or liquefied petrolatum, adding and mixing surfactant into the mixture, adding and mixing water into the mixture, and further mixing the mixture for a sufficient time to homogeneity, such as for at least about 20 minutes.

It should be understood that the wound dressings of the present disclosure are not limited to those illustrated and described herein and alternate wound dressings and components thereof may be utilized. Moreover, wound dressings of the present disclosure may be formed by layering one or more of the same or different wound dressings together to form a three-dimensional structure with any one or more desired dressing properties. For example, any of the layers of structure can utilize any of a substrate formed of woven fibers or yarns, a substrate formed of nonwoven fibers or yarns, and a substrate formed of knitted fibers or yarns.

Example

The following example illustrates embodiments of the present disclosure. The example is illustrative only and is not intended to limit the scope of the present disclosure. Also, parts and percentages are by weight unless otherwise indicated. As used herein, "room temperature" or "ambient temperature" refers to a temperature from about 20° C. to about 25° C.

This example evaluates the efficacy of a wound dressing with oil emulsion, with and without polyhexamethylene biguanide on the biological activity of *Candida Albicans*.

Three samples sets were prepared. Approximately one-inch diameter circular specimens of untreated non-adherent dressing, CURITY™ non-adherent dressing, product code 6121, available from Covidien, Mansfield, Mass., were used for a first sample set, the control set.

A padder/coater from Mathis AG, Oberhasli, Switzerland was used to include polyhexamethylene biguanide into cellulose acetate fabric to produce PHMB-containing fabric for the substrates of the second and third sets. Cellulose acetate fabric was dipped in a polyhexamethylene biguanide solution and then dried with forced air at a temperature in a range of from about 38° C. (about 100° F.) to about 65° C. (about 150° F.); the concentration of the polyhexamethylene biguanide in each of the respective solutions was sufficient to provide about 3,500 ppm of PHMB, for the second set, and about 2,000 ppm of PHMB, for the third set. The dried, PHMB-containing fabric was cut to produce 5 inch by 9 inch substrates for the second and third sets.

An oil emulsion was prepared by heating and mixing about 80 wt % to about 83 wt % white petrolatum, about 15 wt % to about 17 wt % light mineral oil, about 1.5 wt % to about 2.25 wt % sorbitan sesquioleate, and from about 0.5 wt % to about 1 wt % water, at a temperature of from about 40° C. to about 50° C. for about 20 minutes.

Each of the 5 in×9 in substrates of the second and third sets was placed on a conveyer belt. From about 9 g to about 11 g of the prepared oil emulsion was sprayed on each 5 in×9 in substrate by a nozzle along the passing conveyor belt having the substrates to produce the specimen dressings.

Approximately one-inch diameter circular specimens were aseptically cut from the specimen dressings of the first, second, and third sets. Each of the specimens of three sets was aseptically placed on a plate having about 4% trypticase soy agar (TSA), from Sigma-Aldrich, which provided amino acids and nitrogenous substances sufficient for microorganism growth. Different TSA plates were used for different specimens; two specimens of each sample were utilized.

Each of the specimens was inoculated with *Candida albicans* Innoculum samples included the *C. albicans* at a concentration of at least about $10^6$ CFU/mL. Each of the inoculated specimens was incubated at various time intervals, about 24, 48, and 72 hours, at 37° C. After incubation, each of the specimens for each set was aseptically removed from the TSA agar surface and placed into a D/E neutralizing broth, from Fisher Scientific. The neutralizing broth solution was mixed, and serially diluted using phosphate buffered saline according to standard serial dilutions techniques. Biopsies of the agar TSA agar underneath each of the fabric specimens was also performed by removing a portion of the agar (e.g., a plug) and likewise neutralized and analyzed to quantitatively determine the biological activity in the agar.

Figure 17:
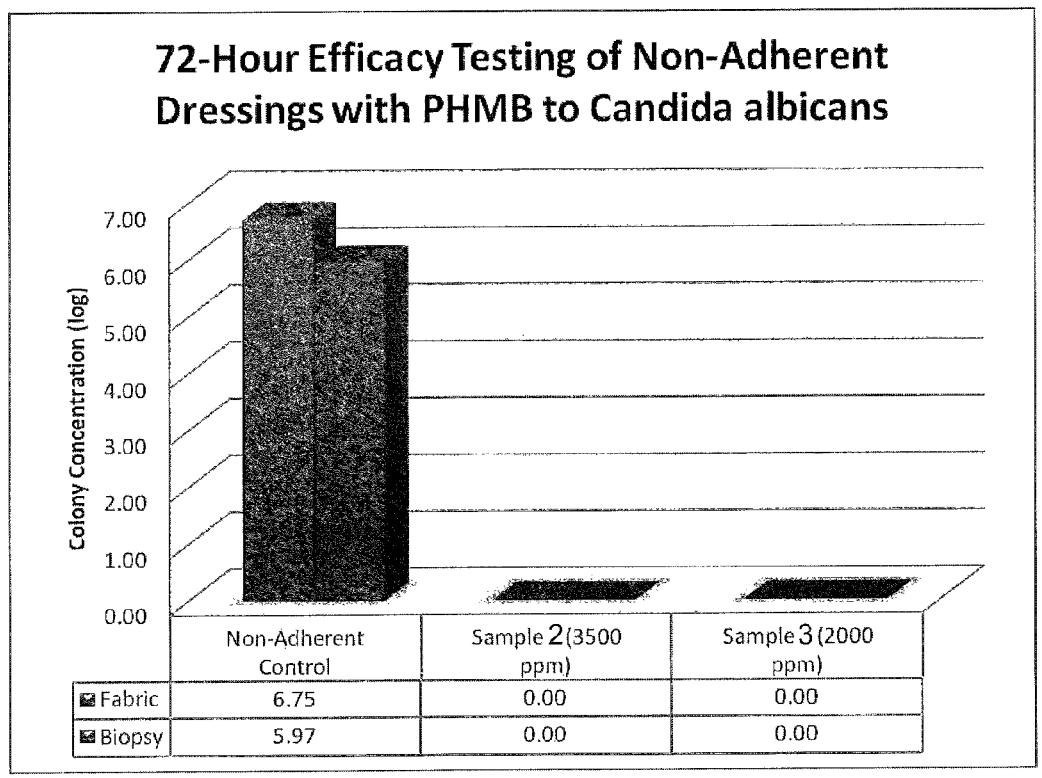
FIG. 17 is a bar graph illustrating antimicrobial efficacy of wound dressings, in accordance with one or more aspects of the present disclosure.

The number of colony forming units was manually counted and the results are summarized in Tables 1 and 2, respectively, and at FIG. 17. Table 1 shows the CFU concentration of *C. albicans* after about 72 hours incubation, followed by dilution and plating. The term "TNTC" is an acronym for "Too Numerous to Count," which denotes plates with colonies more than or equal to 300.

Table 2 shows the concentration of *C. albicans* under the fabric as determined from the biopsies after about 72 hours incubation, followed by dilution and plating. Without any growth on the samples, the thickness of the agar plug provided no change in the growth on the plates.

TABLE 1

Concentration of *C. albicans* on one-inch diameter fabric specimens after 72 hours incubation, then dilution and plating.

| Dilution | Set 1 Non-Adherent Control | | Set 2 3500 ppm PHMB | | Set 3 2000 ppm PHMB | |
|---|---|---|---|---|---|---|
| | 1 | 2 | 1 | 2 | 1 | 2 |
| $10^{-1}$ | TNTC | TNTC | 0 | 0 | 0 | 0 |
| $10^{-2}$ | TNTC | TNTC | 0 | 0 | 0 | 0 |
| $10^{-3}$ | TNTC | TNTC | 0 | 0 | 0 | 0 |
| $10^{-4}$ | TNTC | TNTC | 0 | 0 | 0 | 0 |
| $10^{-5}$ | 72 | 43 | 0 | 0 | 0 | 0 |
| $10^{-6}$ | 9 | 5 | 0 | 0 | 0 | 0 |
| CFU/mL | 7.20E+06 | 4.30E+06 | 0 | 0 | 0 | 0 |
| Log Density | 6.86 | 6.63 | 0 | 0 | 0 | 0 |
| Average, Log Density | 6.75 | | 0 | | 0 | |

TABLE 2

Concentration of *C. albicans* on in agar under one-inch diameter fabric specimens after 72 hours incubation, then dilution and plating.

| Dilution | Set 1 Non-Adherent Control | | Set 2 3500 ppm PHMB | | Set 3 2000 ppm PHMB | |
|---|---|---|---|---|---|---|
| | 1 | 2 | 1 | 2 | 1 | 2 |
| $10^{-1}$ | TNTC | TNTC | 0 | 0 | 0 | 0 |
| $10^{-2}$ | TNTC | TNTC | 0 | 0 | 0 | 0 |
| $10^{-3}$ | TNTC | TNTC | 0 | 0 | 0 | 0 |
| $10^{-4}$ | 103 | 86 | 0 | 0 | 0 | 0 |
| $10^{-5}$ | 9 | 6 | 0 | 0 | 0 | 0 |
| $10^{-6}$ | 0 | 0 | 0 | 0 | 0 | 0 |
| CFU/mL | 1.030E+06 | 8.6E+06 | 0 | 0 | 0 | 0 |
| Log Density | 6.01 | 5.93 | 0 | 0 | 0 | 0 |
| Average, Log Density | 5.97 | | 0 | | 0 | |

FIG. 17 illustrates a logarithmic bar graph of the colony concentration within the control and second and third samples based on the results summarized in Tables 1 and 2. In particular, the graph shows antimicrobial efficacy of the non-adherent dressings of the present disclosure including PHMB on *Candida albicans* even after approximately 72 hours incubation.

Various modifications and variations of the polymers utilized in the wound dressing, as well as configurations of the fibers and yarns of the wound dressing will be apparent to those skilled in the art from the foregoing detailed description. Such modifications and variations are intended to come within the scope of the claims appended hereto. While several embodiments of the disclosure have been described, the disclosure is not limited thereto. Therefore, the above description should not be construed as limiting, but merely as exemplifications of embodiments of the present disclosure.

What is claimed:

1. A wound dressing comprising:
    a substrate comprising a plurality of fibers;
    at least one antimicrobial agent comprising a biguanide in the substrate, wherein the at least one antimicrobial agent is hydrophilic; and
    an oil emulsion impregnated throughout the entire substrate, wherein the oil emulsion consists essentially of:
        a petrolatum in a range of from about 75 wt % to about 90 wt % of the oil emulsion,
        a mineral oil in a range of from about 10 wt % to about 20 wt % of the oil emulsion,
        water in a range of from about 0.1 wt % to about 1 wt % of the oil emulsion, and
        at least one surfactant in a range of from about 1 wt % to about 5 wt % of the oil emulsion.

2. The wound dressing according to claim 1, wherein the at least one surfactant is at least one of:
    an anionic surfactant selected from the group consisting of sodium dodecylsulfate, sodium dodecylbenzene sulfonate, sodium dodecylnaphthalene sulfate, abitic acid, alkyldiphenyloxide disulfonate, sodium dodecylbenzene sulfonate, and combinations thereof;
    a cationic surfactant selected from the group consisting of alkyl benzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, dodecylbenzyl triethyl ammonium chloride, and combinations thereof; or
    a nonionic surfactant selected from the group consisting of polyacrylic acid, methalose, methyl cellulose, ethyl cellulose, propyl cellulose, hydroxyethyl cellulose, carboxymethyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, sorbitan sesquioleate, polyoxyethylene stearyl ether, polyoxyethylene nonylphenyl ether, dialkylphenoxy poly(ethyleneoxy) ethanol, and combinations thereof.

3. The wound dressing according to claim 1, wherein the at least one antimicrobial agent is polyhexamethylene biguanide in a range of from about 500 parts per million (ppm) to about 1,500 ppm on the substrate.

4. The wound dressing according to claim 1, wherein the at least one antimicrobial agent is polyhexamethylene biguanide present in a range of from about 1,500 parts per million (ppm) to about 3,500 ppm on the substrate.

5. The wound dressing according to claim 1, wherein the substrate comprises a plurality of first yarns comprising the plurality of cellulosic fibers and a plurality of second fibers comprising a non-adherent polymeric material selected from the group consisting of polyethylene, polypropylene, polyfluoroethylene, polyfluoropropylene, polyfluoropolyethylene glycol, polytetrafluoroethylene, polyethylene terephthalate, polyethylene naphthalate, polytrimethylene terephthalate, polybutylene terephthalate, and combinations thereof, and wherein an amount of the plurality of cellulosic fibers is in a range of from about 5 wt % to about 50 wt % of the substrate and an amount of the plurality of the second fibers in an amount in a range of from about 50 wt % to about 95 wt % of the substrate.

6. The wound dressing according to claim 1, wherein the substrate consists essentially of cellulosic fibers.

7. The wound dressing according to claim 1, wherein the oil emulsion is present in sufficient amounts to form a barrier that inhibits migration of the antimicrobial agent.

8. A method of preparing a wound dressing, comprising:
applying at least one antimicrobial agent comprising a biguanide on a substrate comprising polymeric fibers, wherein the at least one antimicrobial agent is hydrophilic; and
impregnating an oil emulsion throughout the entire substrate to produce the wound dressing, the oil emulsion consisting essentially of a petrolatum in a range of from about 75 wt % to about 90 wt % of the oil emulsion, a mineral oil in a range of from about 10 wt % to about 20 wt % of the oil emulsion, water in a range of from about 0.1 wt % to about 1 wt % of the oil emulsion, and at least one surfactant in a range of from about 1 wt % to about 5 wt % of the oil emulsion.

9. The method according to claim 8, wherein the substrate consists essentially of cellulosic fiber and polyester, and wherein introducing the oil emulsion comprises impregnating the oil emulsion throughout the entire substrate in an amount of from about 5 wt % to about 75 wt % of the wound dressing.

10. The method according to claim 8, wherein applying the at least one antimicrobial agent comprises exposing the substrate to a solution comprising polyhexamethylene biguanide to provide from about 500 parts per million (ppm) to about 1,500 ppm of the at least one antimicrobial agent on the substrate.

11. The method according to claim 8, wherein applying the at least one antimicrobial agent comprises exposing the substrate to a solution comprising polyhexamethylene biguanide to provide from about 1,500 parts per million (ppm) to about 3,500 ppm of the at least one antimicrobial agent on the substrate.

12. The method according to claim 8, further comprising sterilizing the wound dressing.

13. The method according to claim 8, wherein introducing the oil emulsion comprises introducing the oil emulsion to the substrate in sufficient amounts to form a barrier that inhibits migration of the antimicrobial agent.

\* \* \* \* \*